United States Patent
Blandino et al.

(10) Patent No.: US 10,017,711 B2
(45) Date of Patent: Jul. 10, 2018

(54) (6Z)-NON-6-ENENITRILE AS A FRAGRANCE AND FLAVOR MATERIAL

(71) Applicant: TAKASAGO INTERNATIONAL CORPORATION, Tokyo (JP)

(72) Inventors: Maureen Blandino, North Bergen, NJ (US); Michael E. Lankin, High Bridge, NJ (US); Kent H. Lombard, New York, NY (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 15/024,672

(22) PCT Filed: Sep. 24, 2014

(86) PCT No.: PCT/US2014/057267
§ 371 (c)(1),
(2) Date: Mar. 24, 2016

(87) PCT Pub. No.: WO2015/048163
PCT Pub. Date: Apr. 2, 2015

(65) Prior Publication Data
US 2016/0244693 A1 Aug. 25, 2016

Related U.S. Application Data

(60) Provisional application No. 61/882,475, filed on Sep. 25, 2013.

(51) Int. Cl.
| | | |
|---|---|---|
| C11B 9/00 | (2006.01) |
| A23L 2/56 | (2006.01) |
| A23G 3/36 | (2006.01) |
| A61Q 1/06 | (2006.01) |
| A61Q 5/12 | (2006.01) |
| A61Q 5/02 | (2006.01) |
| A61Q 15/00 | (2006.01) |
| A61Q 9/02 | (2006.01) |
| A61Q 19/10 | (2006.01) |
| A61K 8/40 | (2006.01) |
| C11D 3/50 | (2006.01) |
| C11D 3/26 | (2006.01) |
| A23L 27/20 | (2016.01) |

(52) U.S. Cl.
CPC .............. *C11B 9/0023* (2013.01); *A23G 3/36* (2013.01); *A23L 2/56* (2013.01); *A23L 27/202* (2016.08); *A61K 8/40* (2013.01); *A61Q 1/06* (2013.01); *A61Q 5/02* (2013.01); *A61Q 5/12* (2013.01); *A61Q 9/02* (2013.01); *A61Q 15/00* (2013.01); *A61Q 19/10* (2013.01); *C11D 3/26* (2013.01); *C11D 3/50* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,325,369 A | | 6/1967 | Somerville et al. |
| 4,132,675 A | * | 1/1979 | Naf .......................... C07C 45/40 424/64 |
| 4,280,011 A | | 7/1981 | DeSimone |
| 5,543,536 A | * | 8/1996 | Tam ...................... B01J 31/185 502/162 |
| 5,800,897 A | * | 9/1998 | Sharma .................. A61L 9/042 239/53 |
| 6,123,935 A | * | 9/2000 | Wefler ................... A61L 9/037 219/201 |
| 2004/0116325 A1 | * | 6/2004 | Goodacre ............. C11B 9/0023 512/10 |
| 2008/0032913 A1 | | 2/2008 | Finke et al. |
| 2008/0200363 A1 | | 8/2008 | Smets et al. |
| 2009/0312224 A1 | * | 12/2009 | Yang .................. C11D 17/0026 510/407 |

FOREIGN PATENT DOCUMENTS

| | | |
|---|---|---|
| CN | 102 178 207 A | 9/2011 |
| EP | 1 174 116 A1 | 1/2002 |
| EP | 1 902 632 A1 | 3/2008 |
| WO | WO 2005/037243 A1 | 4/2005 |
| WO | WO 2005/047232 A1 | 5/2005 |

OTHER PUBLICATIONS

APS Narula. The Search for New Fragrance Ingredients for Functional Perfumery. Chemistry and Biodiversity, vol. 1, 2004, pp. 1992-2000.*
APS Narula. The Search for New Ingredients for Functional Perfumery. Chemistry and Biodiversity, vol. 1, 2004, pp. 1992-2000.*
International Search Report dated Dec. 15, 2014 in International Application No. PCT/US14/57267.
Bosma et al., "Homogeneous Metathesis of Unsaturated Nitriles," Journal of the Chemical Society, Chemical Communications, 20:1081-1082 (1981).
Database WPI, Week 201174 Thomson Scientific, London, GB; AN 2011-M95296, XP-002767248.
Supplementary European Search Report dated Feb. 24, 2017 in Application No. EP 14 849 573.2.

* cited by examiner

*Primary Examiner* — Isaac Shomer
*Assistant Examiner* — Michael P Cohen
(74) *Attorney, Agent, or Firm* — Baker Botts L.L.P.

(57) ABSTRACT

The present disclosure provides fragrance and flavor compositions as well as products incorporating such compositions. The disclosed compositions can include (6Z)-non-6-enenitrile of formula (I) and one or more additional fragrance and/or flavor components. The fragrance and flavor compositions of the present disclosure can have appealing, fresh, natural cucumber, melon, and/or violet profiles.

(I)

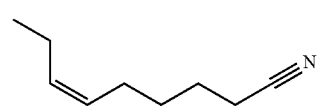

17 Claims, No Drawings

(6Z)-NON-6-ENENITRILE AS A FRAGRANCE AND FLAVOR MATERIAL

CROSS-REFERENCE TO RELATED APPLICATIONS

This application is a U.S. National Stage Patent Application under 35 U.S.C. § 371 of International Application No. PCT/US2014/057267, filed on Sep. 24, 2014, which claims priority under 35 U.S.C. § 119 to U.S. Provisional Application No. 61/882,475, filed Sep. 25, 2013, the contents of each of which are hereby incorporated by reference in their entireties.

FIELD

The presently disclosed subject matter relates to a compound having uses in the fields of fragrances and flavors, as well as compositions containing the compound.

BACKGROUND

There is a continuing interest in the preparation of synthetic fragrance and flavor compounds and their uses in consumer products. Materials that impart violet, green, melon, and cucumber notes, with a low odor threshold, are of particular interest in the fragrance and flavor industry. Compounds that can impart such notes have proven important in many contexts, including air care products (e.g., candles), in personal care products (e.g., lotions and shampoos), in spray perfumes and colognes, in confections, and in beverages.

Several compounds are known in the art for their high impact violet, green, orris, and melon character. For example, certain C9 aldehydes and corresponding nitriles are known for their use in fragrances and flavors to produce such green, melon and violet notes. Specific nitriles have been shown to be more chemically stable than their corresponding aldehydes and thus can have an advantage for use in fragrances and flavors. In certain instances, corresponding nitriles and aldehydes within a given class can have similar flavors and fragrances. However, not all aldehydes and nitriles have been explored for use in the flavor and fragrance industries. Moreover, compared to aldehydes, a relatively small number of nitriles have been accepted for use in the flavor and fragrance industries. The flavor and fragrance properties of many nitriles can be inferior to those of the corresponding aldehydes, as certain nitriles can tend to have more "chemical" and less natural flavors and fragrances.

By way of example, (2E,6Z)-nona-2,6-dienal has been investigated and has been found to have a strong violet leaf, cucumber and watermelon aroma, and is widely used in the flavor and fragrance industry. (2,6)-Nona-2,6-dienenitrile, the corresponding nitrile, was described by BASF in 1984 (DE 102004009440), while its various stereoisomers have been described for their use as flavor and/or fragrance materials (see, e.g., WO 2006/095200; U.S. Pat. No. 8,007,849; WO 2011/128340; DE 2733857).

(2E)-Non-2-enal (EP1262473) has also been explored and has been found to have an extremely strong, very fatty, oily, waxy orris aroma. Its corresponding nitrile, (2E)-Non-2-enenitrile, known as "Iris Nitrile," has been cited in the patent literature for its use in the fragrance industry (EP 1884555; WO 2003/070871; DE 10212687).

Additionally, (6Z)-non-6-enal is used in flavor and fragrance compositions for its strong, natural honeydew and cantaloupe melon notes. The corresponding nitrile, (6Z)-non-6-enenitrile, which has the chemical structure shown below as formula (I), is a known material (CAS#80639-54-9; see U.S. Pat. No. 5,543,536; U.S. Pat. No. 5,688,986; J. Chem. Soc. Chem. Comm. 1981, 1081; and J. Organomet. Chem. 1985, 115).

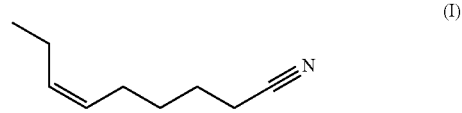

(I)

(6Z)-Non-6-enenitrile is also known as cis-6-noneneni-trile. However, (6Z)-non-6-enenitrile has never been used as a fragrance or flavor compound, and its olfactory, aroma, and flavor properties have not previously been documented.

While structurally similar compounds can, in some circumstances, have similar flavor and fragrance properties, their behavior can be unpredictable. Moreover, the stability of untested flavor and fragrance compounds (and of organic compounds generally) can be difficult to predict.

Existing aldehydes and nitriles used as fragrance and flavor compounds can lack fresh, natural aromas and flavors. Certain existing aldehydes and nitriles used as fragrance and flavor compounds can be chemically unstable in certain media, which can limit their incorporation into products. For example, certain existing aldehydes and nitriles can be unstable in bleaches, unstable in products with high pH, and/or unstable in products with low pH. Thus, there remains a need for chemically stable fragrance and flavor compounds that can help to create fresh, natural aromas and flavors.

SUMMARY

An exemplary fragrance composition includes (6Z)-non-6-enenitrile and one or more additional fragrance components.

In certain embodiments, the fragrance composition can include (6Z)-non-6-enenitrile in an amount from 0.1 ppm to 500,000 ppm, by weight. In certain embodiments, the fragrance composition can include (6Z)-non-6-enenitrile in amount from 0.1 ppm to 1000 ppm, by weight. In certain embodiments, the fragrance composition can include (6Z)-non-6-enenitrile in amount from 1 ppm to 300 ppm, by weight.

In certain embodiments, fragrance compositions of the present disclosure can be incorporated into a product. In certain embodiments, the products can be one or more perfumes, colognes, air fresheners, candles, personal care products, cosmetics, detergents, fabric care products, and household cleaning agents. The air fresheners can be electronic air care devices. The personal care products can be one or more soaps, deodorants, shampoos, conditioners, shower gels, and shaving lotions. The cosmetics can be one or more creams, lotions, ointments, oils, sprays, powders, gels, polishes, and lipsticks. The household cleaning agent can be a bleach.

An exemplary flavor composition includes (6Z)-non-6-enenitrile and one or more additional flavor components.

In certain embodiments, the flavor composition can include (6Z)-non-6-enenitrile in an amount from 0.001 ppm to 50,000 ppm, by weight. In certain embodiments, the flavor composition can include (6Z)-non-6-enenitrile in an amount from 0.001 ppm to 10 ppm, by weight. In certain embodiments, the flavor composition can include (6Z)-non-6-enenitrile in an amount from 0.005 ppm to 0.05 ppm, by weight.

In certain embodiments, flavor compositions of the present disclosure can be incorporated into a product. In certain embodiments, the products can be one or more foods, beverages, confectionaries, oral care products, pharmaceuticals, and gelatinous materials. The beverages can be one or more alcoholic beverages, soft drinks, juices, teas, and flavored waters. The confectionaries can be one or more candies and gums. The oral care products can be one or more toothpastes and mouthwashes.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

DETAILED DESCRIPTION

There remains a continuing need for chemically stable fragrance and flavor compounds that can help to create fresh, natural aromas and flavors, including cucumber and melon aromas and flavors. There also remains a need for fragrance and flavor compositions including such compounds, and for products incorporating such fragrance and flavor compositions. The present disclosure provides an evaluation of (6Z)-non-6-enenitrile, a compound with excellent chemical stability and useful and unexpected fragrance and flavor properties. The present disclosure further provides fragrance and flavor compositions that include (6Z)-non-6-enenitrile as well as products incorporating such fragrance and flavor compositions.

For clarity, and not by way of limitation, the detailed description is divided into the following subsections: 1. Definitions; II. (6Z)-Non-6-enenitrile; Fragrance Compositions and Products; and IV. Flavor Compositions and Products.

I. Definitions

As used herein, the words "a" or "an," when used in conjunction with the term "comprising" in the claims and/or the specification, may mean "one," but they are also consistent with the meaning of "one or more," "at least one," and/or "one or more than one." Furthermore, the terms "having," "including," "containing" and "comprising" are interchangeable, and one of skill in the art will recognize that these terms are open ended terms.

As used herein, the term "about" or "approximately" means within an acceptable error range for the particular value as determined by one of ordinary skill in the art, which will depend in part on how the value is measured or determined, i.e., the limitations of the measurement system.

For example, "about" can mean a range of up to 20%, up to 10%, up to 5%, and or up to 1% of a given value.

While both terms "fragrance" and "flavor" are used herein, it should be understood that compounds that can have beneficial fragrance properties can also have beneficial flavor properties, and vice versa. Accordingly, the terms "fragrance" and "flavor" are not mutually exclusive but instead can each encompass both fragrance and flavor. A "fragrance composition" or a "flavor composition" can have both fragrance and flavor properties and can be synonymous with a "flavor and fragrance composition." Fragrance can also be known as aroma.

While both terms "fragrance product" and "flavor product" are used herein, it should be understood that certain products that can be used as fragrance products can also be used as flavor products, and vice versa. Accordingly, the two types of products are not mutually exclusive. A "fragrance product" or a "flavor product" can have both fragrance and flavor properties and can be synonymous with a "flavor and fragrance product."

As used herein, the term "ppm" means "parts per million." For example, a composition that includes a particular component in an amount of 1 ppm, by weight, includes one unit of the component per million units of the composition, by weight. Measurements in ppm can be converted to other measurements. For example, a particular component present in a composition in an amount of 1 ppm, by weight, can also be expressed as being present in an amount of 1 microgram per gram and/or in an amount of 0.0001%, by weight.

As used herein, the term "aldehyde" means an organic compound having a —C(O)H moiety.

As used herein, the term "nitrile" means an organic compound having a —CN moiety.

II. (6Z)-Non-6-enenitrile (6Z)-Non-6-enenitrile is a C9 nitrile compound having the structure of formula (I):

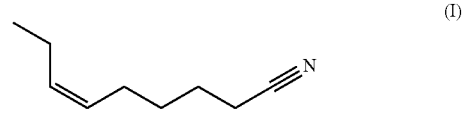

(I)

(6Z)-Non-6-enenitrile (formula (I)) and other nitriles can be prepared by several synthetic routes. For example, for small-scale preparation of (6Z)-non-6-enenitrile, commercially available aldehyde (6Z)-non-6-enal can be treated with ammonium hydroxide and iodine to obtain the nitrile in one step (as disclosed in Org. Lett. 11:1999-2002 (2009)). Alternatively, a cost-effective two-step procedure based on a procedure described in PCT/P2013/063960 (published as WO/2013/176088) can be followed, wherein (6Z)-non-6-enal is converted to an oxime with hydroxylamine.hydrogen chloride and then dehydrated to the nitrile with potassium phosphate. Further details of the preparation and characterization of (6Z)-non-6-enal are provided in the Examples.

It has now been discovered that, when used in fragrance and/or flavor compositions, (6Z)-non-6-enenitrile has certain advantages over other fragrance and flavor compounds. For example, (6Z)-non-6-enenitrile has improved chemical stability as compared to other compounds, e.g., aldehydes. Specifically, (6Z)-non-6-enenitrile has improved stability under acidic conditions, basic conditions, and oxidizing conditions as compared to other compounds. (6Z)-Non-6- enenitrile also has improved stability on exposure to alcohol. These properties make (6Z)-non-6-enenitrile suitable for use in numerous contexts, e.g., in acidic products such as carbonated beverages and fabric softeners, in basic products such as soaps, in oxidizing products such as bleaches, and in products containing alcohol such as alcoholic beverages. Further details of the stability of (6Z)-non-6-enenitrile are provided in the Examples.

(6Z)-Non-6-enenitrile has certain advantageous properties when combined in flavor or fragrance compositions with one or more additional flavor or fragrance components. As noted in the Examples below, (6Z)-non-6-enenitrile is effective in producing appealing flavors and/or fragrances when combined with other flavor and fragrance compounds, including other compounds with cucumber, melon, and/or violet characteristics.

III. Fragrance Compositions and Products

The presently disclosed subject matter provides fragrance compositions including nitrile compounds. An exemplary fragrance composition can include (6Z)-non-6-enenitrile. In certain embodiments, fragrance compositions can include (6Z)-non-6-enenitrile in an amount from about 0.1 ppm to about 500,000 ppm, by weight. In certain embodiments, a fragrance composition can include (6Z)-non-6-enenitrile in amount from about 0.1 ppm to about 1000 ppm, by weight. In certain embodiments, a fragrance composition can include (6Z)-non-6-enenitrile in amount from about 1 ppm to about 300 ppm, by weight. By way of non-limiting example, in certain embodiments a fragrance composition can include (6Z)-non-6-enenitrile in amount from about 0.1 ppm to about 0.5 ppm, from about 0.1 ppm to about 1 ppm, from about 0.1 ppm to about 10 ppm, from about 1 ppm to about 100 ppm, from about 1 ppm to about 200 ppm, from about 10 ppm to about 1000 ppm, from about 100 ppm to about 1000 ppm, from about 1 ppm to about 5 ppm, from about 5 ppm to about 10 ppm, from about 10 ppm to about 20 ppm, from about 20 ppm to about 50 ppm, from about 50 ppm to about 100 ppm, from about 100 ppm to about 200 ppm, from about 200 ppm to about 500 ppm, or from about 500 ppm to about 1000 ppm, by weight.

In certain embodiments, fragrance compositions can further include one or more additional fragrance components. The additional fragrance components can be other flavor and/or fragrance compounds. For example, additional fragrance components can include, but are not limited to, various esters, terpenes, aldehydes, ketones, ethers, nitriles, essential oils, other aromatics, and combinations thereof. In certain embodiments, the additional fragrance components can be compounds that can impart fruity notes. By way of non-limiting example, (6Z)-non-6-enenitrile can be combined with esters to provide fragrance compositions with fruity, ripe melon aromas.

In certain embodiments, (6Z)-non-6-enenitrile can be incorporated into a composition in a diluted form, i.e., mixed with a diluent. The diluent can be a solvent. By way of non-limiting example, suitable solvents that can be used as diluents in fragrance compositions can include benzyl benzoate, isopropyl myristate, propylene glycol, dipropylene glycol, dipropylene glycol methyl ether acetate (DOWANOL™ DPMA), triethyl citrate (TEC), and combinations thereof.

(6Z)-Non-6-enenitrile can be used in fragrance compositions. For example, fragrance compositions that include even small quantities of (6Z)-non-6-enenitrile can possess freshly sliced cucumber, melon, and/or violet aromas with exceptionally high impact. That is, (6Z)-non-6-enenitrile can impart freshly sliced cucumber, melon, and/or violet aromas to a fragrance. (6Z)-Non-6-enenitrile can exhibit highly diffusive character. (6Z)-Non-6-enenitrile can be highly potent and can be used at relatively low concentration (e.g., less than 100 ppm, less than 50 ppm, less than 20 ppm, less than 10 ppm, or less than 5 ppm by weight). For example, as shown in the Examples below, (6Z)-non-6-enenitrile can be incorporated into a fragranced bleach composition at a concentration of 2.5 ppm (0.00025% by weight). When used in a cucumber fragrance, (6Z)-non-6-enenitrile can impart a more well-rounded, natural cucumber aroma. Those skilled in the art will be able to employ (6Z)-non-6-enenitrile at a desired concentration to provide a desired fragrance and intensity.

In certain embodiments, fragrance compositions of the present disclosure can be incorporated into various fragrance products. By way of non-limiting example, the products can be one or more perfumes, colognes, air fresheners, candles, personal care products, cosmetics, detergents, fabric care products, and household cleaning agents. The air fresheners can be one or more sprays, plug in products, gel-type air fresheners, membrane-type air fresheners, nebulizers, diffusers, and potpourris. The air fresheners can be electronic air care devices. By way of non-limiting example, the fragrance compositions of the present disclosed subject matter can be used in conjunction with fragrance delivery devices of U.S. Pat. No. 8,695,891 and U.S. Patent Application Publication No. 2010/0269826, the disclosures of which are hereby incorporated by reference. The candles can be one or more paraffin wax candles, beeswax candles, soy-based candles, tallow candles, and gel candles. The personal care products can be one or more soaps, deodorants, shampoos, conditioners, shower gels, and shaving lotions. The cosmetics can be one or more creams, lotions, ointments, oils, sprays, powders, gels, polishes, and lipsticks. The household cleaning agents can be one or more wipe solutions, cleaning solutions, scrubs, polishes, or bleaches. In certain embodiments, the household cleaning agent can be a fragranced bleach.

Products incorporating fragrance compositions of the present disclosure can have appealing properties. In certain embodiments, products incorporating fragrance compositions of the present disclosure can have appealing, fresh, natural cucumber, melon, and/or violet profiles. Further details of products incorporating fragrance compositions of the present disclosure are provided in the Examples.

IV. Flavor Compositions and Products

The presently disclosed subject matter also provides flavor compositions that include nitrile compounds. An exemplary flavor composition includes (6Z)-non-6-enenitrile. In certain embodiments, flavor compositions can include (6Z)-non-6-enenitrile in an amount from about 0.001 ppm to about 50,000 ppm, by weight. In certain embodiments, a flavor composition can include (6Z)-non-6-enenitrile in an amount from about 0.001 ppm to about 10 ppm, by weight. In certain embodiments, a flavor composition can include (6Z)-non-6-enenitrile in an amount from about 0.005 ppm to about 0.05 ppm, by weight. By way of non-limiting example, in certain embodiments a flavor composition can include (6Z)-non-6-enenitrile in amount from about 0.001 ppm to about 0.005 ppm, from about 0.001 ppm to about 0.01 ppm, from about 0.001 ppm to about 0.1 ppm, from about 0.01 ppm to about 0.1 ppm, from about 0.01 ppm to about 1 ppm, from about 0.01 ppm to about 10 ppm, from about 1 ppm to about 10 ppm, from about 10 ppm to about 50 ppm, from about 50 ppm to about 100 ppm, from about 100 ppm to about 1000 ppm, from about 0.005 ppm to about 0.01 ppm, from about 0.01 ppm to about 0.02 ppm, from about 0.015 ppm to about 0.025 ppm, from about 0.02 ppm to about 0.03 ppm, or from about 0.03 ppm to about 0.05 ppm. In certain embodiments, (6Z)-non-6-enenitrile may be used to prepare flavor concentrates or other concentrated flavor compositions. In such compositions, it should be understood that the concentration of (6Z)-non-6-enenitrile can be higher than in other less concentrated flavor compositions.

The composition can further include one or more additional flavor components. For example, additional flavor components can include, but are not limited to, natural flavors, artificial flavors, acids, bases, amino acids, salts, sweeteners, esters, terpenes, aromatics, and combinations thereof. In certain embodiments, the additional flavor components can be compounds that can impart fruity and/or melon notes. By way of non-limiting example, (6Z)-non-6-enenitrile can be combined with melonal, 3,6-nonadienol, cis-3-nonenal, and/or 2,6-nonadienal to provide compositions with natural, fresh watermelon flavor.

In certain embodiments, (6Z)-non-6-enenitrile can be incorporated into a composition in a diluted form, i.e., mixed with a diluent. The diluent can be a solvent. By way of non-limiting example, suitable solvents that can be used as diluents in flavor compositions can include water, propylene glycol, triglycerides, ethanol, triacetin, glycerol, and combinations thereof.

(6Z)-Non-6-enenitrile can be used in flavor compositions. For example, flavor compositions that include even small quantities of (6Z)-non-6-enenitrile can possess appealing cucumber and/or melon notes. (6Z)-Non-6-enenitrile can be useful in flavor compositions with a cucumber, watermelon, honeydew, and/or cantaloupe flavor profile. It has been discovered that (6Z)-non-6-enenitrile imparts a desirable rind-like or "rindy" note that is not available from other known materials, including (6Z)-non-6-enal. (6Z)-Non-6-enenitrile can be highly potent and can be used at relatively low concentration (e.g., less than about 0.1 ppm, less than about 0.05 ppm, less than about 0.03 ppm, less than about 0.01 ppm, less than about 0.005 ppm, less than about 0.003 ppm, less than about 0.001 ppm, less than about 0.0005 ppm, or less than about 0.0003 ppm by weight). A taste threshold evaluation by expert flavorists demonstrated that (6Z)-non-6-enenitrile can be detected in water at a concentration of 0.0002 ppm.

For example, as shown in the Examples below, (6Z)-non-6-enenitrile can enhance the flavor of a watermelon-flavored beverage when incorporated at about 0.02 ppm, by weight. When used in a watermelon-flavored product, e.g., a food or beverage, (6Z)-non-6-enenitrile can impart a more well-rounded, natural watermelon flavor that includes notes of watermelon rind. Example 6 demonstrates that a watermelon-flavored beverage incorporating (6Z)-non-6-enenitrile was unanimously preferred by a panel of six expert testers to an otherwise identical beverage that did not contain (6Z)-non-6-enenitrile. Those skilled in the art will be able to employ (6Z)-non-6-enenitrile at a desired concentration to provide a desired flavor and intensity.

In certain embodiments, flavor compositions of the present disclosure can be incorporated into various flavor products. In certain embodiments, the products can be one or more foods, beverages, confectionaries, oral care products, pharmaceuticals, and gelatinous materials. The beverages can be one or more alcoholic beverages, soft drinks, juices, teas, flavored waters, and powdered beverage mixes. The confectionaries can be one or more candies and gums. The oral care products can be one or more toothpastes and mouthwashes.

Products incorporating flavor compositions of the present disclosure can have appealing properties. In certain embodiments, products incorporating flavor compositions of the present disclosure can have appealing, fresh, natural cucumber, melon, and/or violet profiles. Further details of products incorporating flavor compositions of the present disclosure are provided in the Examples.

EXAMPLES

The presently disclosed subject matter will be better understood by reference to the following Examples, which are provided as exemplary of the invention, and not by way of limitation. Abbreviations have the usual meaning in the art. The temperatures are indicated in degrees centigrade (° C.). The NMR spectral data were recorded in CDCl$_3$ with a 400 MHz machine for $^1$H and $^{13}$C. The chemical displacements are indicated in ppm with respect to TMS as the standard. The abbreviation "TEC" denotes triethyl citrate. The abbreviation "DPG" denotes dipropylene glycol.

Odor evaluations (e.g., floral, melon) were made by a panel of expert perfumers or at least one expert perfumer.

Example 1: Synthesis of (6Z)-non-6-enal oxime

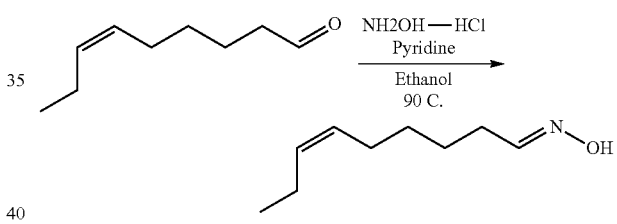

NH$_2$OH.HCl (13.92 g, 0.2 mol, 1.7 eq.) was placed in a 1 L flask equipped with an addition funnel and a condenser. The flask was purged and flushed with N$_2$. At room temperature, ethanol (330 mL) was added, followed by pyridine (19.0 mL, 18.6 g, 0.235 mol, 2.0 eq.) and then (6Z)-non-6-enal (16.5 g, 0.118 mol). The mixture was heated at 90° C. (bath temperature) for 2.5 hours. Upon cooling, the ethanol was removed under reduced pressure, and the remaining material diluted with 200 mL H$_2$O. The solution was extracted with ethyl acetate (2×100 mL), washed with 1N HCl and then brine. The crude material was dried over MgSO$_4$, filtered and concentrated under reduced pressure. Bulb-to-bulb distillation (0.23 T, 60° C.) gave 15.25 g of the oxime, which was used without further purification for the next step.

Example 2: Synthesis of (6Z)-non-6-enenitrile

The oxime of Example 1 (15.25 g), xylenes (90 mL) and K$_3$PO$_4$ (1.5 g, 1% wt. of the oxime) were combined in a 250 mL flask equipped with a Dean-Stark trap and heated at 180° C. (bath temperature) for approximately 9 hours. The reaction was cooled to room temperature, quenched with H$_2$O (100 mL) and extracted with ethyl acetate (2×100 mL). The organic extracts were dried over MgSO$_4$, filtered and concentrated under reduced pressure to 50 g of a yellow oil, still containing xylenes. Simple distillation provided 10.0 g of product (96.3% pure; crude yield=74.6%).

Distillation (0.23 T, 46° C.) provided 4.45 g of the nitrile (99.8% pure, isolated yield=33.0%). Odor at 1% in TEC (repeated with multiple expert perfumers): Fresh sliced crisp cucumber, aquatic, violet leaf, green and floral. GC/MS (EI): m/z (%) 137 (M+), 136, 122 (M+−15), 108, 94, 80, 69, 55, 41. 1H NMR (CDCl3): δ 5.36 (2H, m), 2.33 (2H, t), 2.05 (4H, m), 1.66 (4H, m), 0.93 (3H, t); 13C NMR (CDCl3): δ 132.6, 127.6, 119.7, 28.5, 26.0, 24.8, 20.5, 17.0, 14.2.

Example 3: Alternate Procedure for the Synthesis of (6Z)-non-6-enenitrile (Small Scale)

(6Z)-Non-6-enal (1 g) was diluted in 80 mL THF. $NH_4OH$ 14.3 M (7.5 mL, 15 eq.), was added, followed by $I_2$ (2.0 g, 1.1 eq.). After 1.5 hours, the reaction was quenched with 100 mL 10% $Na_2S_2O_3$. After extracting 2×50 mL with ethyl acetate and drying over $MgSO_4$, the extracts were concentrated to ~2 g yellow oil. Kugelrohr distillation (0.6 T, 60° C.) provided 0.7 g of the nitrile (72.16% yield).

Example 4: Stability Testing of (6Z)-non-6-enenitrile

Stability testing of (6Z)-non-6-enal and (6Z)-non-6-enenitrile was conducted according to the following procedures. Samples of fabric softener, hair color product, shampoo, body soap, and bleach were obtained. The fabric softener was DOWNY® Free, a commercial product containing water, diethyl ester dimethyl ammonium chloride, and starch. The fabric softener had a pH of 3.1. The hair color product was L'OREAL® hair color base, a product containing water, ammonium thioglycolate, and oleic alcohol. The hair color product had a pH of 8.44. The shampoo was a product containing water, triethanolamine lauryl sulfate (TEA lauryl sulfate), and ammonium lauryl sulfate. The shampoo had a pH of 5.66. The body soap was BRADFORD® Tallow 85/15 soap. A 1% solution of the body soap, by weight, in water was prepared, and the pH of the solution was 11.0. The bleach was CLOROX® bleach, a commercial product containing water and sodium hypochlorite. The bleach had a pH of about 12.

Individual samples of (6Z)-non-6-enal and (6Z)-non-6-enenitrile in the fabric softener, hair color product, shampoo, body soap, and bleach were then prepared. (6Z)-Non-6-enal and (6Z)-non-6-enenitrile were added as 1% solutions in TEC, by weight, to separate samples of fabric softener at concentrations ("Dosages") of 0.004% (40 ppm), by weight, of the aldehyde and nitrile. (6Z)-Non-6-enal and (6Z)-non-6-enenitrile were added as 1% solutions in TEC, by weight, to separate samples of hair color product at concentrations ("Dosages") of 0.004% (40 ppm), by weight, of the aldehyde and nitrile. (6Z)-Non-6-enal and (6Z)-non-6-enenitrile were added as 1% solutions in TEC, by weight, to separate samples of shampoo at concentrations ("Dosages") of 0.005% (50 ppm), by weight, of the aldehyde and nitrile. (6Z)-Non-6-enal and (6Z)-non-6-enenitrile were added as 1% solutions in TEC, by weight, to separate samples of body soap at concentrations ("Dosages") of 0.01% (100 ppm), by weight, of the aldehyde and nitrile. (6Z)-Non-6-enal and (6Z)-non-6-enenitrile were added as 1% solutions in TEC, by weight, to separate samples of bleach at concentrations ("Dosages") of 0.00025% (2.5 ppm), by weight, of the aldehyde and nitrile. Individual samples of (6Z)-non-6-enal and (6Z)-non-6-enenitrile in alcohol solution were also prepared by adding the compounds as 1% solutions in TEC, by weight, to separate volumes of 95% ethanol at concentrations ("Dosages") of 0.1% (1000 ppm) by weight. Control samples of the fabric softener, hair color product, shampoo, body soap, bleach, and alcohol without any added compound were also prepared.

The samples of (6Z)-non-6-enal and (6Z)-non-6-enenitrile as well as the control samples were then subjected to various temperatures for a period of four weeks. One set of samples was subjected to a temperature of 5° C. A second set of samples was subjected to ambient temperature ("RT," approximately 20° C.). A third set of samples was subjected to a temperature of 45° C. The samples were then tested for appearance (color change) and odor after four weeks. Appearance was determined by a panel of four expert perfumers according to a five-tier qualitative ranking system: Evaluation Criteria for Color: C1=No Change, C2=Very Slight Change, C3=Slight Change, C4=Change, and C5=Significant Change. Odor was determined by the panel of four expert perfumers according to a five-tier qualitative ranking system: Evaluation Criteria for Odor: No Change, P2=Very Slight Change, P3=Slight Change, P4=Change, and P5=Significant Change. The results of testing are shown in Tables 1 and 2.

TABLE 1

Appearance after 4 weeks:

| | Base | | | | | | | | | | | | | | | | | |
|---|---|---|---|---|---|---|---|---|---|---|---|---|---|---|---|---|---|---|
| | Fabric softener | | | Hair color product | | | Shampoo | | | Body soap | | | Alcohol solution | | | Bleach | | |
| | Dosage | | | | | | | | | | | | | | | | | |
| | 0.004% | | | 0.004% | | | 0.005% | | | 0.01% | | | 0.1% | | | 0.00025% | | |
| Sample | 5° C. | RT | 45° C. | 5° C. | RT | 45° C. | 5° C. | RT | 45° C. | 5° C. | RT | 45° C. | 5° C. | RT | 45° C. | 5° C. | RT | 45° C. |
| Blank (control) | C1 | C1 | C1 | C1 | C1 | C1 | C1 | C1 | C1 | C1 | C1 | C1 | C1 | C1 | C1 | C1 | C1 | C1 |
| (6Z)-Non-6-enenitrile (added as 1% solution (wt %) in TEC) | C1 | C1 | C1 | C1 | C1 | C1 | C1 | C1 | C1 | C1 | C1 | C1 | C1 | C1 | C1 | C1 | C1 | C1 |

TABLE 2

Odor after 4 weeks:

| | Base | | | | | | | | | | | | | | | | | |
|---|---|---|---|---|---|---|---|---|---|---|---|---|---|---|---|---|---|---|
| | Fabric softener | | | Hair color product | | | Shampoo | | | Body soap | | | Alcohol solution | | | Bleach | | |
| | Dosage | | | | | | | | | | | | | | | | | |
| | 0.004% | | | 0.004% | | | 0.005% | | | 0.01% | | | 0.1% | | | 0.00025% | | |
| Sample | 5° C. | RT | 45° C. | 5° C. | RT | 45° C. | 5° C. | RT | 45° C. | 5° C. | RT | 45° C. | 5° C. | RT | 45° C. | 5° C. | RT | 45° C. |
| Blank (control) | P1 | P1 | P2 | P1 | P1 | P2 | P1 | P1 | P2 | P1 | P1 | P2 | P1 | P1 | P2 | P1 | P1 | P2 |
| (6Z)-Non-6-enenitrile (added as 1% solution (wt %) in TEC) | P1 | P1 | P2 | P1 | P1 | P2 | P1 | P1 | P2 | P1 | P2 | P2 | P1 | P1 | P2 | P2 | P3 | P4 |
| (6Z)-Non-6-enal (added as 1% solution (wt %) in TEC) | P2 | P3 | P4 | P2 | P4 | P5 | P2 | P4 | P5 | P2 | P4 | P5 | P1 | P3 | P4 | P2 | P4 | P5 |

Hypochlorite stability testing of (6Z)-non-6-enal and (6Z)-non-6-enenitrile was also conducted, according to the following procedures. The NaClO content of the CLOROX® bleach as well as the NaClO content of the samples of (6Z)-non-6-enal and (6Z)-non-6-enenitrile in bleach (prepared as described above to concentrations of 0.00025% by weight) were tested. Samples to be analyzed were first thoroughly mixed. Then, 2 g of sample was weighed for analysis into a 250 ml Erlenmeyer flask. Subsequently, 15 mL of 10% KI (potassium iodide) and 5 mL of $H_2SO_4$ 2.5 M were added to flask, and the resulting mixture was stirred thoroughly. Free iodine was then titrated with 0.1 N sodium thiosulfate until yellow color disappeared, and the volume of sodium thiosulfate solution added was recorded.

Calculations: Weight % NaClO=((volume sodium thiosulfate, in mL)×(normality of sodium thiosulfate solution)×37.22×100)÷(Sample weight, in grams×1000).

The initial concentration (weight %) of NaClO in the CLOROX® bleach was determined to be approximately 4.5% according to the above procedure.

Stability of the samples of (6Z)-non-6-enal and (6Z)-non-6-enenitrile in bleach was measured after four weeks by determining NaClO concentration (weight %) according to the above procedure. The results of testing are shown in Table 3.

TABLE 3

| | Percentage of NaClO degraded | | |
|---|---|---|---|
| Sample | 5° C. | RT | 45° C. |
| Blank (bleach control) | 3.19% | 7.68% | 18.18% |
| (6Z)-Non-6-enenitrile in bleach (added as 1% solution (wt %) in TEC) | 3.47% | 9.45% | 21.44% |
| (6Z)-Non-6-enal in bleach (added as 1% solution (wt %) in TEC) | 3.59% | 9.87% | 24.02% |

The data of Tables 1, 2, and 3 indicate that (6Z)-non-6-enenitrile is stable under a variety of conditions. Table 1 shows that (6Z)-non-6-enenitrile was sufficiently stable that no change of color (discoloration) was observed in any of the samples containing the compound even after heating to 45° C. for four weeks. According to the panel of four expert perfumers, (6Z)-non-6-enenitrile had a strong and relatively stable fragrance over four weeks, across all of the samples tested. The fragrance of samples containing (6Z)-non-6-enenitrile was found to be different from the fragrance of corresponding samples containing (6Z)-non-6-enal. Samples containing (6Z)-non-6-enenitrile had more fresh sliced cucumber character, with ripe and sweet notes, while samples containing (6Z)-non-6-enal had more honeydew, melon, and green character.

Table 2 shows that (6Z)-non-6-enenitrile had equal or better stability as compared to (6Z)-non-6-enal in all samples tested: fabric softener, hair color product, shampoo, body soap, alcohol solution, and bleach. At ambient temperature and at 45° C., (6Z)-non-6-enenitrile had improved stability under acidic conditions as compared to (6Z)-non-6-enal, as shown in the fabric softener and shampoo results of Table 2. At ambient temperature and at 45° C., (6Z)-non-6-enenitrile also had improved stability under basic conditions as compared to (6Z)-non-6-enal, as shown in the hair color product and body soap results of Table 2. At ambient temperature and at 45° C., (6Z)-non-6-enenitrile also had improved stability under basic and oxidizing conditions as compared to (6Z)-non-6-enal, as shown in the bleach results of Table 2. Moreover, at ambient temperature and at 45° C., (6Z)-non-6-enenitrile had improved stability on exposure to alcohol (ethanol) as compared to (6Z)-non-6-enal, as shown in the alcohol solution results of Table 2.

Table 3 shows that (6Z)-non-6-enenitrile has improved stability to sodium hypochlorite bleach as compared to (6Z)-non-6-enal. Reduced degradation of NaClO was observed in samples containing (6Z)-non-6-enenitrile as compared to samples containing (6Z)-non-6-enal. After four weeks at room temperature, 9.45% of NaClO in the sample of bleach containing (6Z)-non-6-enenitrile had degraded, as compared to 9.87% of NaClO in the sample of bleach containing (6Z)-non-6-enal. After four weeks at 45° C., 21.44% of NaClO in the sample of bleach containing (6Z)-non-6-enenitrile had degraded, as compared to 24.02% of NaClO in the sample of bleach containing (6Z)-non-6-enal.

Example 5: Flavor Composition

The composition presented in Table 4 provided a watermelon-flavored beverage.

TABLE 4

| Component | Quantity (by weight) |
|---|---|
| Water | 92.93% |
| Sugar | 7.00% |
| Citric Acid | 0.05% |
| *Watermelon Flavor | 0.02% |
| Cis-6-Nonenenitrile | 0.02 ppm |

The Watermelon Flavor in Table 4 contained the following ingredients, as presented in Table 5.

TABLE 5

Composition of Watermelon Flavor:

| Component | Quantity (by weight) |
|---|---|
| Propylene Glycol | 99.492% |
| Ethyl Butyrate | 0.160% |
| Melonal | 0.140% |
| Ethyl Acetate | 0.080% |
| Nonadienol 3,6 | 0.040% |
| Isobutyl acetate | 0.040% |
| Nonenal Cis-3 | 0.030% |
| Ethyl Caproate | 0.010% |
| Hexenol Cis-3 | 0.004% |
| Nonadienal 2,6 | 0.002% |
| 6-Methyl-5-hepten-2-one | 0.002% |

The composition of Table 4 was evaluated by a panel of six flavor experts. The composition of Table 4 had an appealing, natural cucumber and melon flavor, with notes of cucumber and watermelon rind. By contrast, a beverage containing all of the components of Table 4 at the given concentrations but without (6Z)-non-6-enenitrile was found to have a more artificial, more typical, less natural cucumber melon flavor. The panel's evaluation results are presented in Table 6. As shown in Table 6, the composition of Table 4 (Sample B), which incorporates (6Z)-non-6-enenitrile at 0.02 ppm, was preferred unanimously to an otherwise identical composition (Sample A) that lacked (6Z)-non-6-enenitrile.

TABLE 6

Results of testing of the composition of Table 4 by a panel of six flavor experts.

| Sample # | Contains (6Z)-Non-6-enenitrile | Overall Summary of Comments | Number of experts who preferred this sample |
|---|---|---|---|
| A | No | sweet, tart, artificial, ripe, green | 0 |
| B | Yes | rindy, fresh, more natural, tart, balanced, peely, green, juicy | 6 |

| Expert # | Sample | Individual Expert Comments |
|---|---|---|
| 1 | A | ripe, fruity watermelon |
|   | B | more rindy, fresh watermelon |

TABLE 6-continued

Results of testing of the composition of Table 4 by a panel of six flavor experts.

| | | |
|---|---|---|
| 2 | A | sweet, lightly watermelon, slightly metallic aftertaste |
|   | B | weaker than A, more cucumber than melon, pleasant salty, mouthwatering aftertaste |
| 3 | A | sweet, tart, mild watermelon, artificial |
|   | B | more natural, tart watermelon/honeydew |
| 4 | A | nice ripe melon, creamy |
|   | B | more preferred, well, balance, slight peely |
| 5 | A | aroma: weaker, green, fatty flavor: heavier green notes, more aldehydic, rind notes |
|   | B | aroma: green, rindy, fatty, fresh pungent flavor: green, fresh, juicy, fresh watermelon |
| 6 | A | very good, balanced, sweet |
|   | B | very good, but more rindy, peely |

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in, the art that various modifications and variations can be made in the compounds and compositions of the disclosed subject matter without departing from the spirit or scope of the disclosed subject matter. Thus, it is intended that the disclosed subject matter include modifications and variations that are within the scope of the appended claims and their equivalents.

What is claimed is:

1. A fragrance composition comprising (6Z)-non-6-enenitrile and one or more additional fragrance components.

2. The fragrance composition of claim 1, wherein the composition comprises (6Z)-non-6-enenitrile in an amount from 0.1 ppm to 500,000 ppm, by weight.

3. The fragrance composition of claim 2, wherein the composition comprises (6Z)-non-6-enenitrile in an amount from 0.1 ppm to 1000 ppm, by weight.

4. The fragrance composition of claim 3, wherein the composition comprises (6Z)-non-6-enenitrile in an amount from 1 ppm to 300 ppm, by weight.

5. The fragrance composition of any one of claims 1-4, wherein the fragrance composition is incorporated into a product selected from the group consisting of perfumes, colognes, air fresheners, candles, personal care products, cosmetics, detergents, fabric care products, and household cleaning agents.

6. The fragrance composition of claim 5, wherein the product is personal care product selected from the group consisting of soaps, deodorants, shampoos, conditioners, shower gels, and shaving lotions.

7. The fragrance composition of claim 5, wherein the product is a cosmetic selected from the group consisting of creams, lotions, ointments, oils, sprays, powders, gels, polishes, and lipsticks.

8. The fragrance composition of claim 5, wherein the air freshener is an electronic air care device.

9. The fragrance composition of claim 5, wherein the household cleaning agent is a bleach.

10. A flavor composition comprising (6Z)-non-6-enenitrile and one or more additional flavor components.

11. The flavor composition of claim 10, wherein the composition comprises (6Z)-non-6-enenitrile in an amount from 0.001 ppm to 50,000 ppm, by weight.

12. The flavor composition of claim 11, wherein the composition comprises (6Z)-non-6-enenitrile in an amount from 0.001 ppm to 10 ppm, by weight.

13. The flavor composition of claim 12, wherein the composition comprises (6Z)-non-6-enenitrile in an amount from 0.005 ppm to 0.05 ppm, by weight.

14. The flavor composition of any one of claims 10-13, wherein the flavor composition is incorporated into a product selected from the group consisting of foods, beverages, confectionaries, oral care products, pharmaceuticals, and gelatinous materials.

15. The flavor composition of claim 14 wherein the product is a beverage selected from the group consisting of alcoholic beverages, soft drinks, juices, teas, and flavored waters.

16. The flavor composition of claim 14, wherein the product is a confectionery selected from the group consisting of candies and gums.

17. The flavor composition of claim 14, wherein the product is an oral care product selected from the group consisting of toothpastes and mouthwashes.

* * * * *